United States Patent [19]

Phillipps et al.

[11] 3,981,894
[45] Sept. 21, 1976

[54] CHEMICAL COMPOUNDS

[75] Inventors: Gordon H. Phillipps, Wembley; Brian M. Bain, Chalfont St. Peter; John C. Clark, Gerrards Cross, all of England

[73] Assignee: Glaxo Laboratories Limited, Greenford, England

[22] Filed: Aug. 29, 1975

[21] Appl. No.: 608,982

[30] Foreign Application Priority Data

Aug. 30, 1974 United Kingdom............... 38089/74

[52] U.S. Cl..................... 260/397.1; 260/239.55 R; 260/397.45
[51] Int. Cl.². ............................................ C07J 3/00
[58] Field of Search ................................. 260/397.1

[56] References Cited
UNITED STATES PATENTS 3,828,080  8/1974  Phillipps et al. ............... 260/239.55

*Primary Examiner*—Elbert L. Roberts
*Attorney, Agent, or Firm*—Bacon & Thomas

[57] ABSTRACT

The specification describes new anti-inflammatory steroids having the formula

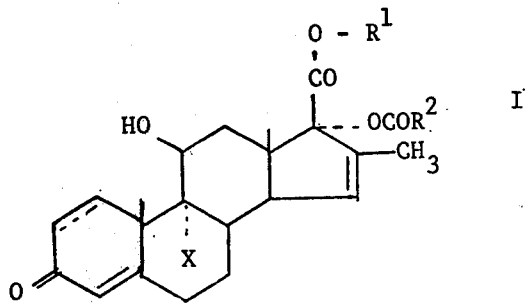

wherein $R^1$ represents a $C_{1-4}$ alkyl or halo- $C_{1-4}$ alkyl group, $R^2$ represents a methyl, ethyl, n-propyl or iso-propyl group (an ethyl group being especially preferred), X represents a hydrogen, chlorine or fluorine atom and $=\!=\!=$ represents a single or double bond.

The specification describes processes for the preparation of such compounds as well as pharmaceutical compositions containing these compounds.

9 Claims, No Drawings

CHEMICAL COMPOUNDS

The present invention relates to novel anti-inflammatory steroids of the androstane series.

Some anti-inflammatory androstane steroids have been described in the literature but research into these compounds has concentrated exclusively on the preparation of steroids having a saturated carbon-carbon bond between the 15- and 16-positions.

We have now surprisingly discovered a new class of androstane steroids having a 16-methyl group and a 15,16- double bond which possess a high level of anti-inflammatory activity, on both internal and topical application. This new class of steroids may be represented by the general formula:

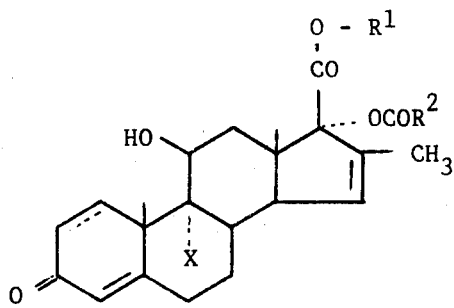

I wherein $R^1$ represents a $C_{1-4}$ alkyl or halo- $C_{1-4}$ alkyl group, $R^2$ represents a methyl, ethyl, n-propyl or isopropyl group (an ethyl group being especially preferred), X represents a hydrogen, chlorine or fluorine atom and $=$ represents a single or double bond.

In formula I above, the halogen substituent, where present in $R^1$, is preferably chlorine or fluorine. The halo- $C_{1-4}$ alkyl group represented by $R^1$ preferably contains a single halogen substituent. Particularly preferred groups are the methyl, chloromethyl and fluoromethyl groups. Other groups which may be represented by $R^1$ include bromomethyl and 2-fluoroethyl groups. X preferably represents a hydrogen or fluorine atom.

Particularly preferred compounds of formula I on account of their especially high anti-inflammatory activity upon topical or internal administration are the methyl, chloromethyl and fluoromethyl esters of $9\alpha$-fluoro-$11\beta$-hydroxy-$16$-methyl-$3$-oxo-$17\alpha$-propionyloxyandrosta-$1,4,15$-triene-$17\beta$-carboxylic acid.

The above compounds of formula I may be prepared for example by esterifying a corresponding $17\alpha$-hydroxy-$17\beta$-carboxylate ester or $17\alpha$-acyloxy-$17\beta$-carboxylic acid, (or functional equivalent thereof) which may itself be prepared from the parent $17\alpha$-hydroxy-$17\beta$-carboxylic acid.

For example $17\beta$-carboxylic acids having the formula I but in which $R^1$ is hydrogen, may be esterified in known manner to provide $17\beta$-carboxylate esters according to the invention. In order to prepare a $C_{1-4}$ alkyl ester the $17\beta$-carboxylic acid may, for example, be reacted with an appropriate diazoalkane, e.g. diazomethane, the reaction being preferably effected in a solvent medium, e.g. ether, tetrahydrofuran or methanol, and at a low temperature, preferably at −5° to +30°C. Alternatively, the $17\beta$-carboxylic acid may be reacted with an appropriate O-alkyl-N,N'-dicyclohexyl-isourea e.g. O-t-butyl-N,N'dicyclohexyl-isourea, preferably in an aprotic solvent such as ethyl acetate, and advantageously at a temperature of 25°–100°C.

Alternatively, a salt of the parent $17\beta$-carboxylic acid for example, an alkali metal e.g. lithium, sodium or potassium, salt or a quaternary ammonium, e.g. triethylammonium or tetrabutylammonium, salt may be reacted with an appropriate alkylating agent, for example, an alkyl halide e.g. the iodide, or a sulphonyloxy compound including a dialkyl sulphate such s dimethyl-sulphate, preferably in a polar solvent medium such as a ketone e.g. acetone or methylethyl ketone, or an amide solvent e.g. dimethyl formamide or hexamethyl phosphoramide, conveniently at a temperature in the range 25° – 100°C. The reaction with an alkyl halide may conveniently be employed to prepare the ethyl and propyl $17\beta$-carboxylate esters according to the present invention.

The esterification of $17\alpha$-hydroxy-$17\beta$-carboxylates is preferably effected using an appropriate anhydride under basic conditions, e.g. in pyridine or triethylamine, and with a 4-(disubstituted-amino)-pyridine such as 4-dimethylaminopyridine or 4-pyrrolidinopyridine as catalyst. Usually acylation of the $11\beta$-hydroxy group will also occur and selective hydrolysis will be required.

For the preparation of the $17\alpha$-esters of the $17\beta$-carboxylic acids which may be employed in the preparation of the compounds according to the invention, it is often preferred to treat the parent $17\alpha$-hydroxy $17\beta$-carboxylic acid with the appropriate carboxylic acid anhydride, if desired in the presence of a base such as potassium carbonate. Any mixed anhydrides formed may be solvolysed under acidic (e.g. aqueous acetic acid) or basic (e.g. aqueous pyridine or diethylamine-/acetone) conditions. Alternatively, the parent $17\alpha$-hydroxy compound may be treated with the appropriate carboxylic acid chloride, preferably in a solvent such as an halogenated hydrocarbon e.g. methylene chloride, and advantageously in the presence of a base such as triethylamine, preferably at a low temperature e.g. 0°C.

$\Delta^{15}$-$17\alpha$-hydroxy starting materials may be prepared for example by subjecting a compound of formula

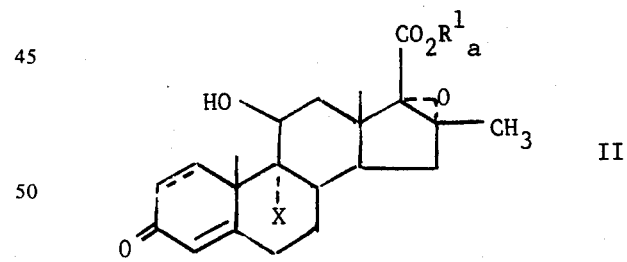

II (wherein X and $=$ are as hereinbefore defined and $R^1_a$ represents a hydrogen atom or a $C_{1-4}$ alkyl or halo-$C_{1-4}$ alkyl group) to an epoxide ring-opening reaction, to produce a compound of formula

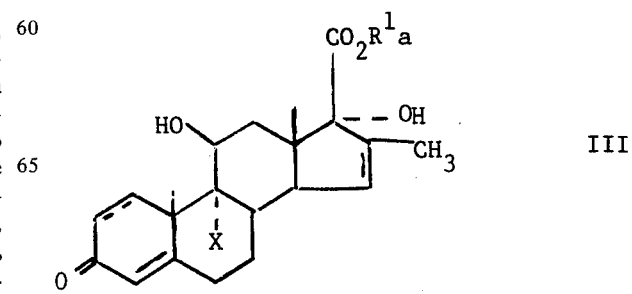

III

The above-mentioned epoxide ring-opening reaction is preferably effected under acid conditions using for example a hydrogen halide such as hydrogen chloride, hydrogen bromide or hydrogen iodide. The reaction is conveniently effected in a polar medium e.g. tetrahydrofuran, the medium advantageously being aqueous. The desired 16-methyl-15-ene can be separated at this stage from any concomitantly formed 16-methylene isomer; such separation can be effected in conventional manner e.g. by fractional crystallisation or chromatography. The unpurified mixture can alternatively be subjected to the above mentioned subsequent esterification step before separation is effected. Preferably, $R^1_a$ in the compound of formula II is hydrogen.

The above compounds of formula II may be prepared by epoxidation of the corresponding 16-ene compound e.g. by reaction with an epoxidation agent such as a per-acid, e.g. peroxytrifluoroacetic acid, preferably in a solvent medium comprising for example methylene chloride, the epoxidation advantageously being effected in the presence of an excess of disodium hydrogen phosphate. The 16-ene used as starting material in the last-mentioned process, may be prepared for example from the corresponding 16-methyl-20-keto-21-hydroxy-16-ene by oxidative removal of the 21-carbon atom in conventional manner, e.g. by reaction with periodic acid as described for example in Belgian Patent No. 778,285. The resulting 17-carboxylic acid produced in accordance with this method may, if desired, be esterified to produce a corresponding $C_{1-4}$ alkyl or halo-$C_{1-4}$ alkyl 17-carboxylate, e.g. as described above for the esterification of $\Delta^{15}$-17$\beta$-carboxylic acids.

The above-mentioned 16-methyl-20-keto-21-hydroxy-16-ene may be prepared for example by reaction of the corresponding 16-methyl-17,21-dihydroxy-20-keto-pregnane steroid, the process comprising first forming a 3,20-bis-semicarbazone, and then effecting elimination of water whereby the desired 16-ene is formed, the latter stage advantageously being effected using hot aqueous acetic acid with simultaneous loss of the semi-carbazone groups.

For the preparation of those compounds of formula I wherein $R^1$ represents a halo-$C_{1-4}$ alkyl group, the esterification generally referred to above can be carried out in an analogous manner to that described above for the preparation of the $C_{1-4}$ alkyl esters, for example, by reacting a salt of the parent 17$\beta$-carboxylic acid with a compound $R^1$—Z where Z is an appropriate displaceable substituent e.g. a halogen atom or a sulphonyloxy group such as a mesyloxy or tosyloxy group. Where Z is a halogen atom it is preferably iodine. This method is particularly applicable to the preparation of those compounds of formula I wherein $R^1$ represents a chloromethyl group, the said halo compound in this case being iodochloromethane.

Those compounds of formula I wherein $R^1$ represents a halo-$C_{1-4}$ alkyl group may also be prepared by reacting a compound of formula

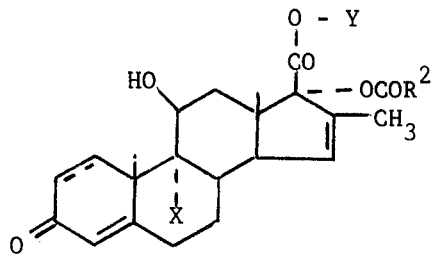

IV (wherein X, $R^2$ and $=$ are as hereinbefore defined and Y represents a $C_{1-4}$ alkyl group substituted by a displaceable radical) with a compound serving to replace the said displaceable radical in the group Y by the desired halogen atom. Y may thus for example, be a chlorine, bromine or iodine atom.

Thus, for example, in accordance with the last-mentioned process iodoalkyl 17$\beta$-carboxylate compounds may be prepared from corresponding chloroalkyl 17$\beta$-carboxylate compounds using for example an alkali metal, alkaline earth metal or quaternary ammonium iodide, e.g. sodium iodide. Similarly, bromoalkyl 17$\beta$-carboxylate compounds may be prepared from corresponding iodoalkyl 17$\beta$-carboxylate compounds using a bromide salt such as lithium bromide. The reaction is advantageously effected in a solvent medium comprising for example acetone, methyl ethyl ketone, dimethylformamide, dimethylacetamide, hexamethylphosphoramide or ethanol.

A similar halogen displacement reaction may be employed to prepare fluoroalkyl 17$\beta$-carboxylate compounds from the corresponding bromo-, chloro- or iodo-alkyl compound, namely reaction with an appropriate fluoride, e.g. silver monofluoride or silver difluoride, conveniently in a solvent, for example acetonitrile. This halogen displacement reaction is particularly advantageous for the preparation of the fluoromethyl and fluoroethyl compounds of formula I.

The new haloalkyl 17$\beta$-carboxylate compounds of formula I can also be prepared by a displacement reaction effected on a corresponding alkyl or aryl sulphonyloxyalkyl, e.g. mesyloxyalkyl, compound by reaction with an alkali metal, alkaline earth metal or quaternary ammonium halide conveniently in a solvent medium, e.g. acetone, dimethyl formamide, hexamethylphosphoramide or ethanol. The sulphonyloxy compound may be prepared for example from a corresponding 2-hydroxyalkyl compound produced, for example, by reaction of a 17$\beta$-carboxylic acid salt with an appropriate halohydrin.

The $\Delta^4$ compounds according to the invention can conveniently be prepared by partial reduction of the corresponding $\Delta^{1,4}$ compound, for example, by hydrogenation using a palladium catalyst, conveniently in a solvent e.g. ethyl acetate or by homogeneous hydrogenation using for example tris(triphenylphosphine)rhodium chloride, conveniently in a solvent such as benzene, or by exchange hydrogenation using for example cyclohexene in the presence of a palladium catalyst in a solvent e.g. ethanol, preferably under reflux. This reduction may be carried out on a haloalkyl ester where this is sufficiently stable in such a reaction or may be effected at an earlier stage.

There are also provided pharmaceutical compositions for use in anti-inflammatory therapy, comprising at least one compound according to the invention together with one or more pharmaceutical carriers or excipients. Such compositions may be in forms adapted for topical or internal administration.

The active androstane compounds may be formulated into preparations suitable for topical administration with the aid of a topical vehicle therefor. Examples of various types of preparation for topical administration, include ointments, lotions, creams, powders, drops, (e.g. eye or ear drops), sprays, (e.g. for the nose or throat), suppositories, retention enemas, chewable or suckable tablets or pellets (e.g. for the treatment of aphthous ulcers) and aerosols. Ointments and creams may for example, be formulated with an aqueous or oily base with the addition of suitable thickening and/or gelling agents and/or glycols. Such a base may thus, for example, include water and/or an oil such as liquid paraffin or a vegetable oil such as arachis oil or castor oil, or a glycolic solvent such as propylene glycol or 1,3-butane-diol. Thickening agents which may be used according to the nature of the base include soft paraffin, aluminium stearate, cetostearyl alcohol, polyethylene glycols, woolfat, hydrogenated lanolin and beeswax and/or glyceryl monostearate and/or non-ionic emulsifying agents.

The solubility of the steroid in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following namely, emulsifying agents, dispersing agents, suspending agents, thickening agents, solvents, colouring agents and perfumes.

Powders may be formed with the aid of any suitable powder base e.g. talc, lactose or starch. Drops may be formulated with an aqueous base also comprising one or more dispersing agents, suspending agents or solubilising agents etc.

Spray compositions may for example be formulated as aerosols with the use of a suitable propellant, e.g. dichlorodifluoromethane or trichlorofluoromethane.

The proportion of active androstane compound in the topical compositions according to the invention depends on the precise type of formulations to be prepared but will generally be within the range of from 0.0001 to 5.0% by weight. Generally however for most types of preparations advantageously the proportion will be within the range of from 0.001 to 0.5% and preferably 0.01 to 0.25%.

Topical preparations may be administered by one or more applications per day to the affected area; over skin areas occlusive dressings may ofen be used with advantage.

For internal administration the new compounds according to the invention may, for example, be formulated for oral, parenteral or rectal administration. For oral administration, syrups, elixirs, powders and granules may be used which may be formulated in conventional manner. Dosage unit forms are however preferred as described below.

For parenteral administration the compounds may be presented in sterile aqueous or oily vehicles, suitable oily vehicles including arachis oil, olive oil etc.

Preferred forms of preparation for internal administration are dosage unit forms i.e. presentations in unitary form in which each unit contains a desired dose of the active steroid. Such dosage unit forms contain from 0.05 to 2.0 mg, preferably from 0.25 to 1.0 mg of the active steroid. For oral administration suitable dosage unit forms include tablets, coated tablets and capsules. For parenteral administration dosage unit forms include sealed ampoules or vials each containing a desired dose of the steroid. Suppositories, which may be prepared for example with conventional commercial suppository bases, provide a dosage unit form for rectal administration. Sterile tablet or pellet implants may also be used, e.g where slow systemic absorption is desired.

The compounds according to the invention may in general be given by internal administration in cases where systemic adreno-cortical therapy is indicated.

In general terms preparations for internal administration may contain from 0.01 to 5.0% of active ingredient dependent upon the type of preparation involved. The daily dose may vary from 0.05 to 10.0 mg. dependent on the condition being treated and the duration of treatment desired.

The compositions according to the invention may also include one or more preservatives or bacteriostatic agents e.g. methyl hydroxy benzoate, propyl hydroxy benzoate, chlorocresol or benzalkonium chlorides. The compositions according to the invention may also contain other active ingredients such as antimicrobial agents, particularly antibiotics, such as neomycin.

The following Examples illustrate the present invention. In these Examples (and also the Preparations) the ultraviolet spectra are in ethanol, unless stated otherwise, and melting points were determined on a Kofler block and are uncorrected. Organic extracts were dried over magnesium sulphate. Temperatures in °C Preparation 1

Betamethasone 3,20-bis-semicarbazone

A mixture of betamethasone (100 g,), semicarbazide hydrochloride (140 g), and sodium bicarbonate (75 g) in methanol (1500ml) and water (88 ml) was heated on a steam bath for 22 hours. Most of the solvent was removed under reduced pressure and the residue was treated with water (1500 ml). The product was collected, washed with water and dried in vacuo over phosphorus pentoxide to give the title compound as an off-white solid (138.6g), $\lambda_{max}$ 241 nm ($\epsilon_{1cm}{}^{1\%}$ 380), 294 nm ($E_{1cm}{}^{1\%}$ 480).

Preparation 2

9α-Fluoro-11β,21-dihydroxy-16-methylpregna-1,4,16-triene-3,20-dione.

A mixture of betamethasone 3,20-bis-semicarbazone (24.5 g) and 50% (1:1 v/v) aqueous acetic acid (1600 ml) was heated on a steam bath under nitrogen for 4 hours. The mixture was cooled to room temperature then treated with aqueous pyruvic acid (70 ml) and kept overnight. The orange mixture was poured into water and the product was extracted with methylene chloride; the organic extracts were washed with water and with saturated sodium bicarbonate solution, then dried (with simultaneous treatment with charcoal) and evaporated to give the title compound as a light brown crystalline solid (14.3g.), $\lambda_{max}$ 243–244 nm ($E_{1cm}{}^{1\%}$ 582).

PREPARATION 3

9α-Fluoro-11β-hydroxy-16-methyl-3-oxoandrosta-1,4,16-triene-17-carboxylic Acid

A suspension of 9α-fluoro-11β,21-dihydroxy-16-methylpregna-1,4,16-triene-3,20-dione (12.24 g) in tetrahydrofuran (120 ml) was stirred with a solution of periodic acid (26.525 g) in water (60 ml) at 19°. A solid crystallised after 30 minutes, and after 90 minutes the reaction mixture was filtered and the solid was washed and dried to give the title acid as small pale yellow needles (10.23 g) as a tetrahydrofuran (0.5 mole) solvate, thin layer chromatography (t.l.c.) $R_F$ 0.3 pink (silica, chloroform:acetone 4:1).

PREPARATION 4

16α,17α-Epoxy-9α-fluoro-11β-hydroxy-16β-methyl-3-oxoandrosta-1,4-diene-17β-carboxylic acid Trifluoroacetic anhydride (37 ml) was added during 15 minutes to a mixture of hydrogen peroxide (5.3 ml of 85% i.e. 6.4 g) in methylene chloride (80 ml) at between 0° and −10°. The solution of peroxytrifluoroacetic acid was added, with stirring, to a suspension of 9α-fluoro-11β-hydroxy-16-methyl-3-oxoandrosta-1,4,16-triene-17-carboxylic acid (18.34 g of tetrahydrofuran solvate) and finely powdered disodium hydrogen phosphate (300 g) in methylene chloride (900 ml), at between 0° and 5° during 5 minutes.

After 40 minutes the suspension was diluted with petroleum ether (bp 60°–80°) and filtered to give a pale yellow solid.

The solid was dissolved in water at ca 40° and the pH was lowered to 3.0 to give a white solid which was filtered, washed, and dried to give the title compound (13.08g). A sample was crystallised from methanol as white needles, m.p. 203° to 206.5° (decomp.), $[\alpha]_D^{18}$ + 66.5° (c 0.960, dioxan), $\lambda_{max}$ 239.5 nm ($\epsilon$ 15,000).

PREPARATION 5

9α-Fluoro-11β,17α-dihydroxy-16-methyl-3-oxoandrosta-1,4,15-triene-17β-carboxylic Acid Powdered 16α,17α-epoxy-9α-fluoro-11β-hydroxy-16β-methyl-3-oxoandrosta-1,4-diene-17β-carboxylic acid (12.6 g) was added during 15 minutes to a solution of concentrated hydrochloric acid (50 ml) in tetrahydrofuran (120 ml) at 0°. The suspension was stirred at 4° for 24 hours then at 22° for 5 hours. The mixture was filtered to give the crude title compound (3.38 g). The filtrate was diluted with water to give a further crop of the acid (5.49 g).

The two crops of crude title compound were fractionally crystallised from aqueous methanol (2 x) then methanol (4 x) to give the title compound (3.61 g) as a mixture of white needles and prisms, m.p. 219° to 237.5° (decomp), $[\alpha]_D^{18}$ −26.5° (c 1.06, dimethyl sulphoxide), $\lambda_{max}$ 239 nm ($\epsilon$ 14,900). By p.m.r. and t.l.c. (silica, developing solvent-upper phase from butanol: ethanol: water (4:1:5) equilibrated at ca 20°) the product contained ca 5 to 10% of the 16-methylene isomer.

PREPARATION 6

9α-Fluoro-11β-hydroxy-16-methyl-3-oxo-17α-propionyloxyandrosta-1,4,15-triene-17β-carboxylic acid A solution of 9α-fluoro-11β,17α-dihydroxy-16-methyl-3-oxoandrosta-1,4,15-triene-17β-carboxylic acid (3.026g, containing ca 5 to 10% of its 16-methylene isomer) and triethylamine (2.95ml) in dry methylene chloride (100 ml) at 0° was treated, dropwise with stirring, with propionyl chloride (1.85 ml) during 10 minutes at below 5°. After 30 minutes at below 5° the reaction mixture was diluted with methylene chloride and washed with sodium bicarbonate solution then water. The organic layer was dried and evaporated to give the intermediate anhydride as a white foam (4.11g).

The foam was stirred with diethylamine (3.1 ml) in acetone (20 ml) at 18° for 20 minutes. Scratching the flask gave the diethylammonium salt of the title acid (3.866 g) which was dissolved in water (200 ml), and acidified to pH 2 to give white curds, which were filtered, washed, and dried to give the title acid (3.087 g).

A sample was crystallised twice from acetone to give the title compound as white prisms, m.p. 147° to 149°C, $[\alpha]_D^{23}$ + 126° (c 0.211, Me$_2$SO), $\lambda_{max}$ 238 nm ($\epsilon$ 15,700), t.l.c. (silica, developing solvent as in Preparation 5) indicating contamination by ca 5–10% of its 16-methylene isomer.

EXAMPLE 1

Chloromethyl 9α-fluoro-11β-hydroxy-16-methyl-3-oxo-17α-propionyloxyandrosta-1,4,15-triene-17β-carboxylate A suspension of 9α-fluoro-11β-hydroxy-16-methyl-3-oxo-17α-propionyloxyandrosta-1,4,15-triene-17β-carboxylic acid (2.732 g, containing ca 5 to 10% of its 16-methylene isomer) in methanol (12 ml) was treated with a solution of sodium hydroxide in methanol (3 ml of 2M-solution at 18°). The acid dissolved and the pH of the solution rose to 8. After 10 minutes, ether (500 ml) was added giving a white solid and the mixture was cooled to 0°. The solid was filtered off, washed and dried to give the sodium salt of the starting material (2.509 g).

The sodium salt was added portion-wise to a solution of chloromethyl iodide (3.5 ml) in hexamethylphosphoramide (10 ml) at 18° during 15 minutes. After 2 hours, reaction was almost complete, and the mixture was diluted with ethyl acetate and washed with dilute sodium thiosulphate solution, water, sodium bicarbonate, water and brine and was dried and evaporated to give a white foam (3.054 g) consisting mainly of the title compound but containing ca 5–10% of its 16-methylene isomer as judged by t.l.c. (silica; benzene — ethyl acetate 5:1).

Part (1.728 g) of the foam was chromatographed on 10 silica plates [20 × 40 cm] developing with benzene: ethyl acetate (10:1; 2×), then chloroform (4×). The main band was eluted with ethyl acetate which was evaporated to give white needles (956 mg) which were rechromatographed on 7 silica plates [20 × 40cm], developing with benzene: ethyl acetate (10:1, 3×; 8:1, 2×; and finally 5:1, 2×). The front half of the main band was eluted with ethyl acetate which was evaporated to give the title compound as needles (470 mg) which were crystallised twice from acetone then once from ethyl acetate to give the title compound as white prisms (151 mg) m.p. 160° to 171°C (decomp). $[\alpha]_D^{20}$ −96.5° (c 0.23, dioxan), $\lambda_{max}$ 239 nm ($\epsilon$ 15,800).

EXAMPLE 2

Fluoromethyl 9α-fluoro-11β-hydroxy-16-methyl-3-oxo-17α-propionyloxyandrosta-1,4,15-triene-17β-carboxylate A solution of chloromethyl 9α-fluoro-11β-hydroxy-16-methyl-3-oxo-17α-propionyloxyandrosta-1,4,15-triene-17β-carboxylate (containing ca 5 to 10% of its 16-methylene isomer by t.l.c. (benzene-ethyl acetate 5:1)1.326 g) was stirred with silver fluoride (3.0 g) in dry acetonitrile (40 ml) for 15 days at 18° in the dark. The black mixture was filtered through kieselguhr which was extracted with ethyl acetate. The solution was washed with water and brine and was dried and evaporated to give a pale yellow foam (1.168 g).

The foam (1.103 g) was chromatographed on 10 silica plates (20 × 40 cm), developing with benzene: ethyl acetate (10:1, 1×; 9:1, 1×; 8:1, 2×; 7:1, 3×). The main band was eluted with ethyl acetate, which was evaporated to give a white foam (740 mg) which was crystallised three times from ethyl acetate to give the title compound as white prisms (424 mg) m.p. 172° to 183°, $[\alpha]_D^{22}$ −124° (c 0.905 dioxan), $\lambda_{max}$ 238.5 nm ($\epsilon$ 15,500).

EXAMPLE 3

Methyl
9α-Fluoro-11β-hydroxy-16-methyl-3-oxo-17α-propionyloxyandrosta-1,4,15-triene-17β-carboxylate A solution of 9α-fluoro-11β-hydroxy-16-methyl-3-oxo-17α-propionyloxyandrosta-1,4,15-triene-17β-carboxylic acid (containing ca 5 to 10% of its 16-methylene isomer) (528 mg,) in acetone (20 ml) was treated with a slight excess of diazomethane in ether (ca 15 ml) at 22°. The solution was treated with acetic acid (ca 0.5 ml) and evaporated to give a foam. The foam was dissolved in methylene chloride which was washed with saturated sodium bicarbonate solution, water, and brine, dried and evaporated to give a foam (545 mg).

The foam was chromatographed on three silica plates (20 × 40 cm) developing with benzene: ethyl acetate (10:1, 6 runs and 7:1, 2 runs). The front three quarters of the main band was eluted with ethyl acetate to give an oil (457 mg) which was crystallised twice from ethyl acetate giving crystals which were dried to give the title compound as white prisms (265 mg) m.p. 186° to 188°, $[\alpha]_D^{22}$ −135° (c 0.865, dioxan), $\lambda_{max}$ 239 nm ($\epsilon$ 15,700).

EXAMPLE 4

Methyl
9α-fluoro-11β-hydroxy-16-methyl-3-oxo-17α-propionyloxy-androsta-4,15-diene-17β-carboxylate

Method A

A solution of 9α-fluoro-11β-hydroxy-16-methyl-3-oxo-17α-propionyloxyandrosta-1,4,15-triene-17β-carboxylic acid (606 mg) and tris(triphenylphosphine)rhodium chloride (596 mg) in methanol (30 ml) and benzene (30 ml) was hydrogenated at 22°/745 mm Hg for two days when tlc showed consumption of starting material (the uptake of hydrogen was 45ml). The solution was evaporated and the solid was partitioned between ethyl acetate (40ml) and 1% sodium carbonate solution (4×10ml). The aqueous layer was acidified and extracted with ethyl acetate, which was washed with water, dried, and evaporated to give a pale yellow foam (340mg), the intermediate 1,2-dihydro-acid.

A solution of the foam (313mg) in dry dimethylacetamide (6ml) was stirred with methyl iodide (0.5ml) sodium bicarbonate (205 mg) and a few pieces of molecular sieve (type 4A; ca. 0.1 g) in the dark at 20° for two hours. The solution was concentrated, poured into water, and extracted into ethyl acetate, which was washed, dried, and evaporated to give a pale yellow foam (326mg).

This was chromatographed on silica, developing with chloroform:acetone (20:1, 8×) and eluting the main band with ethyl acetate to give a white foam (160mg). The foam was crystallised from methanol to give the title compound (56mg), m.p. 180° to 186°, $[\alpha]_D^{22}$ −91° (c 0.540, dioxan), $\lambda_{max}$ 237.5nm ($\epsilon$ 17,300).

Method B

A solution of methyl 9α-fluoro-11β-hydroxy-16-methyl-3-oxo-17α-propionyloxyandrosta-1,4,15-triene-17β-carboxylate (128mg) and tris(triphenylphosphine)rhodium chloride (135mg) in benzene (13 ml) was hydrogenated at 22°/763mm Hg until all the starting material was consumed (22 hours). The solution was evaporated and the mixture was chromatographed on silica developing with chloroform:acetone (14:1; 2×) and eluting with ethyl acetate to give the title compound [154mg, but contaminated with triphenylphosphine oxide (ca. 1.0mole)]. Apart from the triphenylphosphine oxide, the sample resembled (tlc, pmr) the previous sample (method A).

EXAMPLE 5

Fluoromethyl
9α-Fluoro-11β-hydroxy-16-methyl-3-oxo-17α-propionyloxyandrosta-4,15-diene-17β-carboxylate

Method A

A solution of chloromethyl 9α-fluoro-11β-hydroxy-16-methyl-3-oxo-17α-propionyloxyandrosta-1,4,15-triene-17β-carboxylate (772mg) and tris(triphenylphosphine)rhodium chloride (178mg) in benzene (40 ml) and methanol (30 ml) was hydrogenated at 24°/763mm Hg for 7 days. The solution was evaporated to give a brown foam (918mg), which was chromatographed on silica, developing with chloroform:acetone (6:1, 2×). The main band was eluted with ethyl acetate to give the intermediate chloromethyl 1,2-dihydroester as a pale yellow foam (508mg).

A solution of the foam (480mg) was stirred with finely divided silver monofluoride (1.276g) in dry acetonitrile at 22° for 13 days. The reaction mixture was filtered through kieselguhr, which was washed with ethyl acetate. The filtrate and washings were combined and washed with water and brine, dried, and evaporated to give a pale yellow foam (442mg). The foam was chromatographed on silica, developing with chloroform:acetone (40:1, 4×) and the main band was eluted with ethyl acetate to give a white solid (381mg). The solid was crystallised from methanol to give the title compound as white prisms (317mg), m.p. 178° to 184°, $[\alpha]_D^{22}$ −88° (c 0.983, dioxan).

Method B

A solution of fluoromethyl 9α-fluoro-11β-hydroxy-16-methyl-3-oxo-17α-propionyloxyandrosta-1,4,15-triene-17β-carboxylate (290mg) was hydrogenated as in the previous example (Method B) to give a white foam (245mg) which was shown (tlc, pmr) to be the title compound contaminated with triphenylphosphine oxide.

The following Examples illustrate pharmaceutical compositions according to the invention.

| Example A: Water - miscible cream | |
|---|---|
| Active ingredient | 0.1% w/w |
| Beeswax (White) | 15.0% w/w |
| Cetostearyl alcohol B.P.C. | 7.0% w/w |
| Cetomacrogol 1000 B.P.C. | 3.0% w/w |
| Liquid paraffin B.P. | 5.0% w/w |
| Chlorocresol | 0.1% w/w |
| Distilled water to produce | 100 parts by weight |

Ball-mill the steroid with a little liquid paraffin until the particle size is reduced to 95% by number below 5μ. Heat the available water to 100°C, add the chlorocresol, stir to dissolve and cool to 65°C. Melt together the beeswax, cetostearyl alcohol and cetomacrogol and maintain at 65°C. Add the steroid suspension using the remaining liquid paraffin for rinsing. Add the steroid oil phase at 60°C to the chlorocresol aqueous phase at 65°C and stir rapidly while the emulsion cools over the gelling point (40°–45°C). Continue to stir at slow speed until the cream sets.

| Example B: Oral tablet | |
|---|---|
| Active ingredient | 0.5 mg. |
| Lactose | 175.5 mg. |
| Maize starch (dried) | 20.0 mg. |
| Gelatin | 2.0 mg. |
| Magnesium stearate | 2.0 mg. |
| Tween 80 | Trace |
| Total weight | 200.0 mg. |

A suspension of 300 mg. of the active ingredient in 2 ml. of water containing 0.1% of Tween 80 is milled for 16 hours in a 10 ml. nylon pot about three quarters filled with steatite balls until 90% by number of the particles have a diameter of less than 5 microns with none greater than 50 microns. The maize starch and lactose are blended and passed through a 60 mesh B.S. sieve and granulated with a 10% solution of gelatin containing the suspension of the active ingredient and washings from the nylon pot, by passing through a 16 mesh B.S. sieve. The granules are dried at 40°C overnight, passed through a 20 mesh B.S. sieve and blended with magnesium stearate and tabletted using a tabletting machine having a 5/16 inch flat-bevelled punch.

We claim:

1. Compounds of the general formula

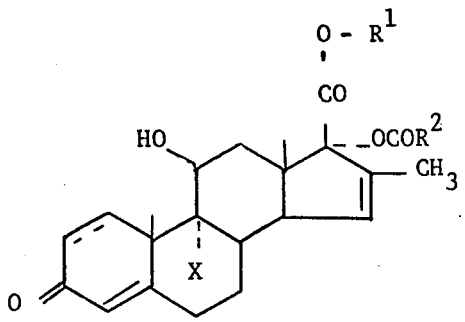

I wherein $R^1$ represents a $C_{1-4}$ alkyl or halo-$C_{1-4}$ alkyl group, $R^2$ represents a methyl, ethyl, n-propyl or isopropyl group, X represents a hydrogen, chlorine or fluorine atom and $\rightleftharpoons$ represents a single or double bond.

2. Compounds as claimed in claim 1 wherein $R^1$ represents a methyl, chloromethyl or fluoromethyl group.

3. Compounds as claimed in claim 1 wherein $R^2$ represents an ethyl group.

4. A compound as claimed in claim 1, said compound being chloromethyl 9α-fluoro-11β-hydroxy-16-methyl-3-oxo-17α-propionyloxyandrosta-1,4,15-triene-17β-carboxylate.

5. A compound as claimed in claim 1, said compound being fluoromethyl 9α-fluoro-11β-hydroxy-16-methyl-3-oxo-17α-propionyloxyandrosta-1,4,15-triene-17β-carboxylate.

6. A compound as claimed in claim 1, said compound being methyl 9α-fluoro-11β-hydroxy-16-methyl-3-oxo-17α-propionyloxyandrosta-1,4,15-triene-17β-carboxylate.

7. A compound as claimed in claim 1, said compound being methyl 9α-fluoro-11β-hydroxy-16-methyl-3-oxo-17α-propionyloxyandrosta-4,15-diene-17β-carboxylate.

8. A compound as claimed in claim 1, said compound being fluoromethyl 9α-fluoro-11β-hydroxy-16-methyl-3-oxo-17α-propionyloxyandrosta-4,15-diene-17β-carboxylate.

9. Pharmaceutical compositions comprising, as active ingredient, at least one compound of formula I (of claim 1) together with at least one pharmaceutical carrier or excipient.

* * * * *